United States Patent
Barshinger et al.

(10) Patent No.: US 9,207,213 B2
(45) Date of Patent: Dec. 8, 2015

(54) METHOD AND APPARATUS FOR INSPECTING AND MONITORING PIPE

(71) Applicant: General Electric Company, Schenectady, NY (US)

(72) Inventors: James Norman Barshinger, State College, PA (US); Mark Howard Feydo, Reedsville, PA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 211 days.

(21) Appl. No.: 13/735,192

(22) Filed: Jan. 7, 2013

(65) Prior Publication Data

US 2014/0190264 A1     Jul. 10, 2014

(51) Int. Cl.
*G01N 29/04* (2006.01)
*G01N 29/22* (2006.01)

(52) U.S. Cl.
CPC ............. *G01N 29/04* (2013.01); *G01N 29/043* (2013.01); *G01N 29/223* (2013.01); *G01N 2291/0289* (2013.01); *G01N 2291/2634* (2013.01); *G01N 2291/2636* (2013.01)

(58) Field of Classification Search
CPC .................................................. G01N 29/04
USPC ........... 73/592, 599, 600, 602, 622, 628, 638
See application file for complete search history.

(56) References Cited

U.S. PATENT DOCUMENTS

| | | | | |
|---|---|---|---|---|
| 4,532,796 A * | 8/1985 | Martens et al. | ................ | 73/632 |
| 5,907,100 A * | 5/1999 | Cook | .............. | 73/602 |
| 6,799,466 B2 * | 10/2004 | Chinn | ............. | 73/622 |
| 6,925,881 B1 | 8/2005 | Kwung et al. | | |
| 7,694,564 B2 * | 4/2010 | Brignac et al. | ................ | 73/596 |
| 8,285,495 B2 * | 10/2012 | Purekar et al. | ................ | 702/39 |
| 8,336,394 B2 * | 12/2012 | Laurent | ..................... | 73/861.29 |
| 8,590,383 B2 * | 11/2013 | Brignac et al. | ................ | 73/640 |
| 8,714,030 B1 * | 5/2014 | Liu et al. | .................... | 73/861.28 |
| 2002/0134161 A1 | 9/2002 | Chinn | | |
| 2003/0188589 A1 | 10/2003 | Harthorn et al. | | |
| 2006/0203086 A1 * | 9/2006 | Pavlakovic | .................... | 348/61 |
| 2014/0202249 A1 * | 7/2014 | Luo et al. | ....................... | 73/597 |

OTHER PUBLICATIONS

PCT Search Report and Written Opinion dated Mar. 12, 2014 issued in connection with corresponding PCT Patent Application No. PCT/US2013/072594.

* cited by examiner

*Primary Examiner* — J M Saint Surin
(74) *Attorney, Agent, or Firm* — Cooper Legal Group, LLC

(57) ABSTRACT

An ultrasonic sensor assembly detects a characteristic of a pipe. The ultrasonic sensor assembly includes first and second transducer rings spaced apart along a length of the pipe. Each of the first and second transducer rings can transmit a first wave longitudinally along the pipe and receive a reflection of the transmitted first wave from the characteristic. The first transducer ring can use results related to the reflection of the transmitted first wave to guide a second wave along the pipe that is received by the second transducer ring. Methods of detecting a characteristic of the pipe are also provided.

20 Claims, 4 Drawing Sheets

METHOD AND APPARATUS FOR INSPECTING AND MONITORING PIPE

BACKGROUND OF THE INVENTION

1. Field of the Invention

The present invention relates generally to ultrasonic sensor assemblies, and more particularly, to an ultrasonic sensor assembly for inspecting and monitoring at least one characteristic of a pipe.

2. Discussion of the Prior Art

Ultrasonic sensor assemblies are known and used in many different applications. Ultrasonic sensor assemblies are used, for example, to monitor/inspect a test object and to detect/identify at least one characteristic of the test object, such as corrosion, defects, thickness, etc. In pipeline corrosion monitoring applications, the test object can include a pipe section. In such an example, one or more ultrasonic sensor assemblies are wrapped around an outer surface of the pipe during inspection.

It has been difficult to simultaneously detect the presence/absence, location, and size of the characteristic. Accordingly, it would be beneficial to provide an ultrasonic sensor assembly that simultaneously detects the presence, location and size of characteristics in the pipe.

BRIEF DESCRIPTION OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect, the present invention provides an ultrasonic sensor assembly for detecting a characteristic of a pipe. The ultrasonic sensor assembly includes a first transducer ring attached to the pipe. A second transducer ring is attached to the pipe at a spaced location from the first transducer ring. Each of the first and second transducer rings transmits a first wave longitudinally along the pipe and receives a reflection of the transmitted first wave from the characteristic. The first transducer ring will use results related to the reflection of the transmitted first wave to guide a second wave along the pipe that is received by the second transducer ring.

In accordance with another aspect, the present invention provides an ultrasonic sensor assembly for detecting a characteristic of a pipe. The ultrasonic sensor assembly includes a first transducer ring attached to the pipe. A second transducer ring is attached to the pipe at a spaced location from the first transducer ring. Each of the first and second transducer rings will transmit a first wave longitudinally along the pipe and receive a reflection of the transmitted first wave reflected from the characteristic. The first transducer ring will use results related to the reflection of the transmitted first wave to guide a second wave along the pipe that is received by the second transducer ring. The waves received by the transducer rings are configured to be analyzed to detect a dimension and location of the characteristic of the pipe.

In accordance with another aspect, the present invention provides a method of detecting a characteristic of a pipe. The method includes the steps of providing an ultrasonic sensor assembly including first and second transducer rings attached to and spaced apart along a length of the pipe. The method includes the step of transmitting one or more first waves into the pipe from each of the first and second transducer rings. The method includes the step of receiving a reflection of the transmitted first wave reflected from the characteristic by the first and second transducer rings. The method includes the step of transmitting one or more second waves into the pipe from the first transducer ring and receiving the one or more second waves with the second transducer ring. The method includes the step of detecting the characteristic of the pipe based on the waves received by each of the first and second transducer rings.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION OF THE INVENTION

Figure 1:
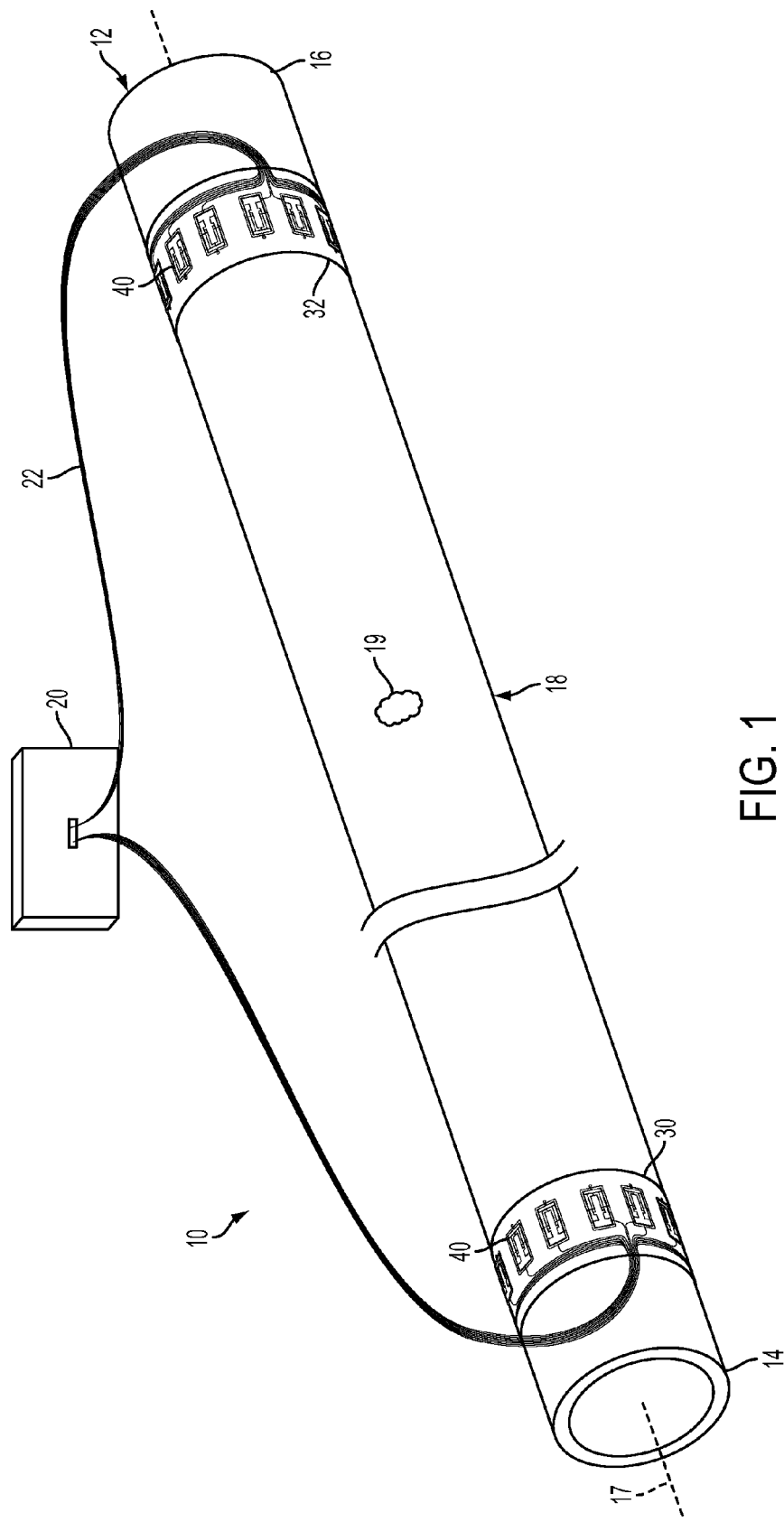
FIG. 1 is a perspective view of an example ultrasonic sensor assembly for use with a pipe in accordance with an aspect of the present invention.

Example embodiment(s) that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

FIG. 1 illustrates a perspective view of an example ultrasonic sensor assembly 10 according to one aspect of the invention. In short summary, the ultrasonic sensor assembly 10 includes a first transducer ring 30 and a second transducer ring 32 spaced apart and attached (temporarily or permanently) to a pipe 12. The first and second transducer rings 30, 32 each transmit and receive ultrasonic waves to detect and locate a characteristic 19 of the pipe 12. In particular, the first and second transducer rings first transmit ultrasonic waves into the pipe 12, and receive respective reflections of the ultrasonic waves from the characteristic 19. Next, the first transducer ring transmits ultrasonic waves through the characteristic 19, and thereafter the ultrasonic waves are received by the second transducer ring. Arrival times (e.g., time of flight, etc.) for the ultrasonic waves are measured to determine a more accurate location and size of the characteristic 19.

The pipe 12 is shown to have a generally cylindrical shape extending between a first end 14 and an opposing second end 16. The pipe 12 can include a non-solid body (e.g., hollow body) or may be solid. It is to be appreciated that the pipe 12 is somewhat generically/schematically depicted in FIG. 1 for ease of illustration. Indeed, the pipe 12 is not limited to extending along a linear axis 17, and may include bends, undulations, curves, or the like. Further, while the pipe 12 is shown to be cylindrical in shape, in other examples, the pipe 12 could include other non-cylindrical shapes and sizes. For example, the pipe 12 could have a non-circular cross-sectional shape, such as by having a square or rectangular cross-section. In other examples, the pipe 12 further includes a tubular shape, conical shape, or the like. As such, the pipe 12 shown in FIG. 1 comprises only one possible example of a pipe.

The pipe 12 could include a wide range of dimensions. For example, the pipe 12 could be longer or shorter in length than as shown (as evidenced by the break in the pipe shown in FIG. 1). Further, the pipe 12 may include a larger or smaller cross-sectional size (e.g., diameter in the shown example). The pipe 12 includes an outer surface 18. The outer surface 18 defines a perimeter length (e.g., circumference) around the pipe 12.

The pipe 12 further includes the characteristic 19. The characteristic 19 is somewhat generically depicted in FIG. 1, as it is to be appreciated that the characteristic 19 includes any number of items that can be detected. In one example, the characteristic 19 includes corrosion in the pipe 12. However, the characteristic 19 is not limited to including corrosion, and may further include imperfections (flaws, cracks, voids, inclusions, etc.), dimensions (wall thickness, length, etc.), and/or the like. The characteristic 19 is not limited to the size, shape, or location that is shown in FIG. 1, and instead could be larger or smaller in size, may be positioned closer to the first end 14 or second end 16 of the pipe 12, and/or may include a plurality of characteristics. Further, the characteristic 19 could be positioned entirely within the walls of the pipe 12, at an inner or outer wall of the pipe 12, etc.

Turning to the test apparatus 20, the test apparatus 20 is somewhat generically/schematically depicted. In general, the test apparatus 20 can include any number of different configurations. In one example, the test apparatus 20 is operatively attached to the first transducer ring 30 and the second transducer ring 32 by means of a wire 22. It is to be appreciated that the term wire is meant to include a multi-wire and/or multi-component wire, and/or a flexible circuit/lead. In further examples, the test apparatus 20 and the transducer rings 30, 32 could communicate wirelessly. As will be described in more detail below, the test apparatus 20 is configured to send and receive information (e.g., data, control instructions, etc.) to/from the transducer rings 30, 32 through the wire 22. This information can be related to the characteristic 19 of the pipe 12. This information includes, but is not limited to, dimensions of the pipe 12 (e.g., thickness, length, etc.), the presence or absence of corrosion for corrosion mapping, cracks, or the like. The test apparatus 20 can include circuits, processors, running programs, memories, computers, power supplies, ultrasound contents, or the like. In further examples, the test apparatus 20 includes a user interface, display, and/or other devices for allowing a user to control the ultrasonic sensor assembly 10.

Figure 2:
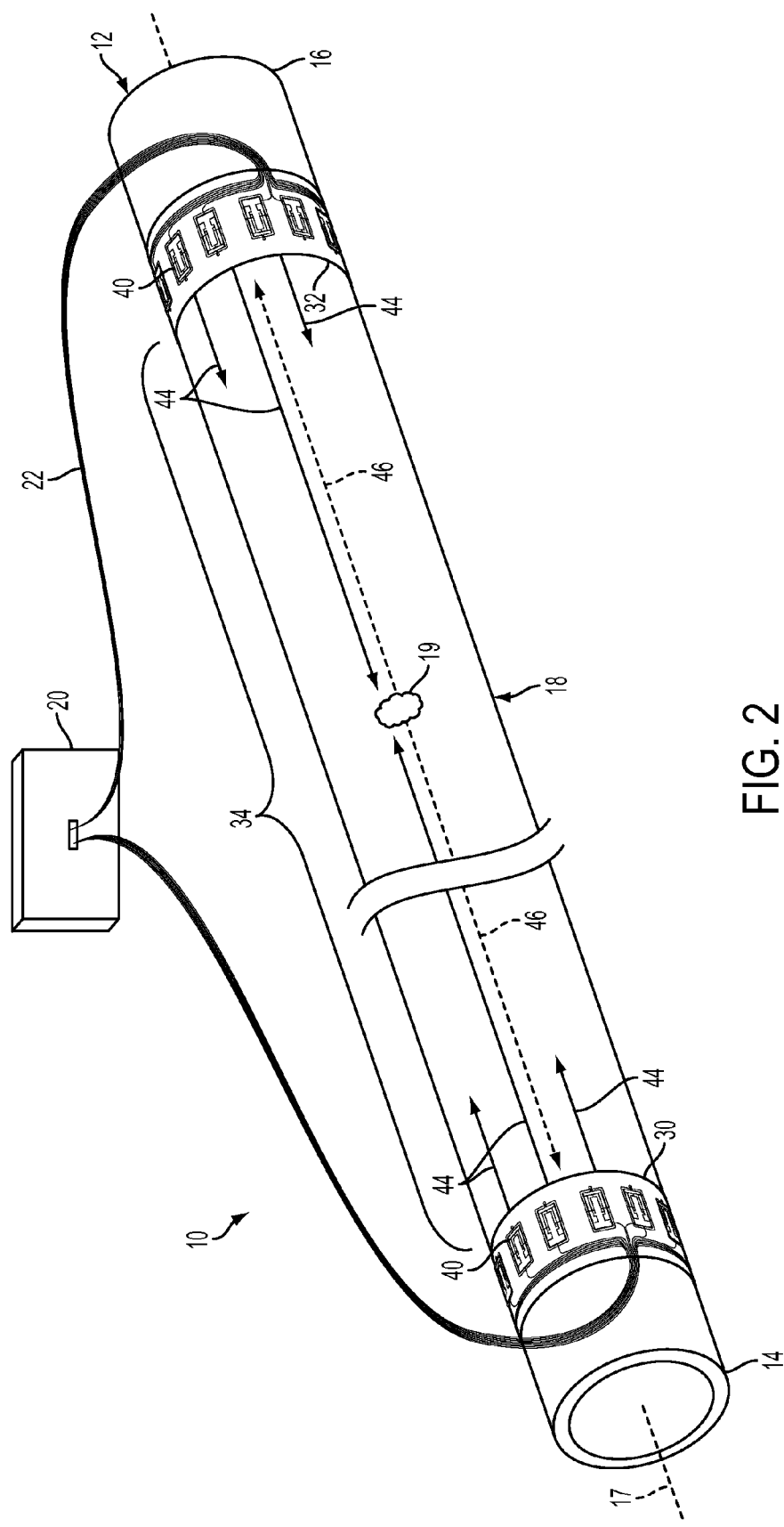
FIG. 2 is a perspective view of the example ultrasonic sensor assembly in operation during a pulse-echo test.

Turning now to FIG. 2, the ultrasonic sensor assembly 10 further includes the first transducer ring 30 and second transducer ring 32. The first transducer ring 30 and second transducer ring 32 can be similar or identical in structure. The transducer rings 30, 32 are spaced apart along the pipe 12 to define an inspection region 34 extending therebetween. In one example, the inspection region 34 has a length that is approximately four times the circumference of the pipe 12. In the shown example, the first transducer ring 30 is positioned towards the first end 14 of the pipe 12 while the second transducer ring 32 is positioned towards the second end 16 of the pipe 12. Of course, in further examples, the transducer rings 30, 32 could be positioned at any number of locations along the pipe 12, such as by being closer towards a center, closer towards the first end 14 or second end 16, etc. Similarly, the transducer rings 30, 32 could be positioned closer together or farther apart, such that the inspection region 34 could be larger or smaller than as shown.

The transducer rings 30, 32 can include a size and shape that substantially matches a size and shape of the pipe 12. For example, the outer surface 18 of the pipe 12 has the circular shape, such that the transducer rings 30, 32 likewise have a matching circular shape. The transducer rings 30, 32 can have a diameter that is slightly larger than a diameter of the pipe 12, such that the transducer rings 30, 32 are in contact with the outer surface 18. Of course, in further examples, the transducer rings 30, 32 are not limited to having the circular cross-section, and in further examples, could have nearly any cross-sectional size and shape that matches the cross-sectional size and shape of the pipe 12. In other examples, the transducer rings 30, 32 including a flexible material that can be wrapped around the pipe 12.

The transducer rings 30, 32 each include a plurality of transducers 40. The transducers 40 are somewhat generically/schematically shown, as it is to be appreciated that the transducers 40 include nearly any size, shape, and configuration. The transducers 40 are provided to extend around each of the transducer rings 30, 32. For example, the first transducer ring 30 includes a plurality of transducers 40 extending around the first transducer ring 30 and in contact with the outer surface 18. Likewise, the second transducer ring 32 includes a plurality of transducers 40 extending around the second transducer ring 32 in contact with the outer surface 18. The transducers 40 can be positioned to extend substantially 360° around the outer surface 18 of the pipe 12.

As is generally known, each transducer ring 30, 32 can be provided with any number of transducers 40. Further, the transducers 40 can be arranged to be closer together or farther apart than as shown. In one particular example, the circumferential transducer 40 spacing is less than half of the ultrasonic wavelength of waves transmitted by the transducers 40. As such, the number of transducers 40 in each of the transducer rings 30, 32 can be approximately double the pipe circumference of the pipe 12 per wavelength. In another example, the transducers may also be arranged in a two-dimensional array. It is to be appreciated that the example presented within the figures depicts only one ring of transducers 40 in each of the first transducer ring 30 and second transducer ring 32. However, the ultrasonic sensor assembly 10 is not limited to including the one ring of transducers 40, and in further examples, could include multiple rings of transducers 40 in either or both of the first transducer ring 30 and second transducer ring 32.

Each of the transducers 40 of the first transducer ring 30 and second transducer ring 32 is capable of transmitting (e.g., sending, conveying, etc.) a wave, pulse, energy, and/or other impulses along the pipe 12. As is generally known, the transducers 40 can transmit longitudinal and/or torsional guided waves. The transducers 40 can likewise receive the wave, pulse, energy, and/or other impulses, such as by receiving a reflection of the wave. In such an example, the transducers 40 can include both a transmitter and a receiver. In other examples, however, each of the transducers 40 is capable of transmitting the wave, pulse, energy, etc. while a second set of transducers is capable of receiving the wave, pulse, energy, etc. It is to be appreciated, however, that the first transducer ring 30 and second transducer ring 32 can each be designed in any number of ways, such that the wave, pulse, energy, and/or other impulses can be both transmitted and received by each of the first transducer ring 30 and second transducer ring 32.

Referring still to FIG. 2, the operation of the ultrasonic sensor assembly 10 will now be described. The ultrasonic sensor assembly 10 will first carry out a pulse-echo test to determine a location of the characteristic 19. During the pulse-echo test, the first transducer ring 30 and second transducer ring 32 are arranged such that the characteristic 19 is positioned within the inspection region 34 between the transducer rings 30, 32. The first transducer ring 30 and second transducer ring 32 will each create and transmit a first wave 44 longitudinally along the pipe 12 into the inspection region 34. It is to be appreciated that the first wave 44 is somewhat generically depicted (as an arrowhead) since the first wave 44 can include a pulse, energy, and/or other impulses.

The first waves 44 will propagate from the transducer rings 30, 32, into the inspection region 34, and towards the characteristic 19. At least some of the first waves 44 will encounter the characteristic 19. The first waves 44 that encounter the characteristic 19 can at least partially reflect from the characteristic 19 in the form of one or more reflections 46 (shown generically with a dashed line arrowhead). These reflections 46, which can include reflecting waves, can generally travel in an opposite direction from the first waves 44. In particular, the first transducer ring 30 transmits the first waves 44 toward the characteristic 19 and receives the reflection(s) 46 back from the characteristic 19. Likewise, the second transducer ring 32 will also transmit the first waves 44 toward the characteristic 19 and receive the reflection(s) 46 back from the characteristic 19. It is to be appreciated that while both transducer rings 30, 32 are shown to produce and transmit the first waves 44, in further examples, only one of the first transducer ring 30 and second transducer ring 32 may produce and transmit the first waves 44.

The reflections 46 from a respective transducer 40 that generated the first wave 44 are received by the transducers 40 in each of the first transducer ring 30 and second transducer ring 32. Information related to the reflections 46 is transmitted to the test apparatus 20. The test apparatus 20 analyzes and evaluates characteristics related to the reflections 46. The test apparatus 20 can analyze, for example, a time of flight, amplitude, velocity change, time shift, etc. of the reflections 46 from the characteristic 19 for each of the first transducer ring 30 and second transducer ring 32.

Based on this analysis and evaluation of characteristics of the reflections 46, the test apparatus 20 draws conclusions as to the location of the characteristic 19 or multiple characteristics. For example, the test apparatus 20 can accurately determine a presence and a location of the characteristic 19 within the pipe 12. In particular, the test apparatus 20 can determine a longitudinal location of the characteristic 19 along a length of the pipe 12. Further, by analyzing the reflections 46 of both the first transducer ring 30 and second transducer ring 32, the longitudinal location of ends of the characteristic 19 can be determined. For example, the longitudinal location of an end of the characteristic 19 closest to the first end 14 of the pipe 12 can be determined based on analyzing the reflections 46 received by the first transducer ring 30. Similarly, the longitudinal location of an opposing end of the characteristic 19 closest to the second end 16 of the pipe 12 can be determined based on analyzing the reflections 46 received by the second transducer ring 32. In a further example, a circumferential location of the characteristic 19 is also determined based on the analysis of the reflections 46 received by the first transducer ring 30 and second transducer ring 32.

The pulse-echo test can relatively accurately determine the presence and location of the characteristic 19 within the pipe 12. However, determining a size of the characteristic 19 with the pulse-echo test is less accurate than determining the presence and location of the characteristic 19. The size of the characteristic 19 includes dimensions of the characteristic 19, such as longitudinal length, circumferential width, depth, or the like. To more accurately determine the size of the characteristic 19, a guided wave tomographic test can be carried out based on the results from the pulse-echo test.

Figure 3:
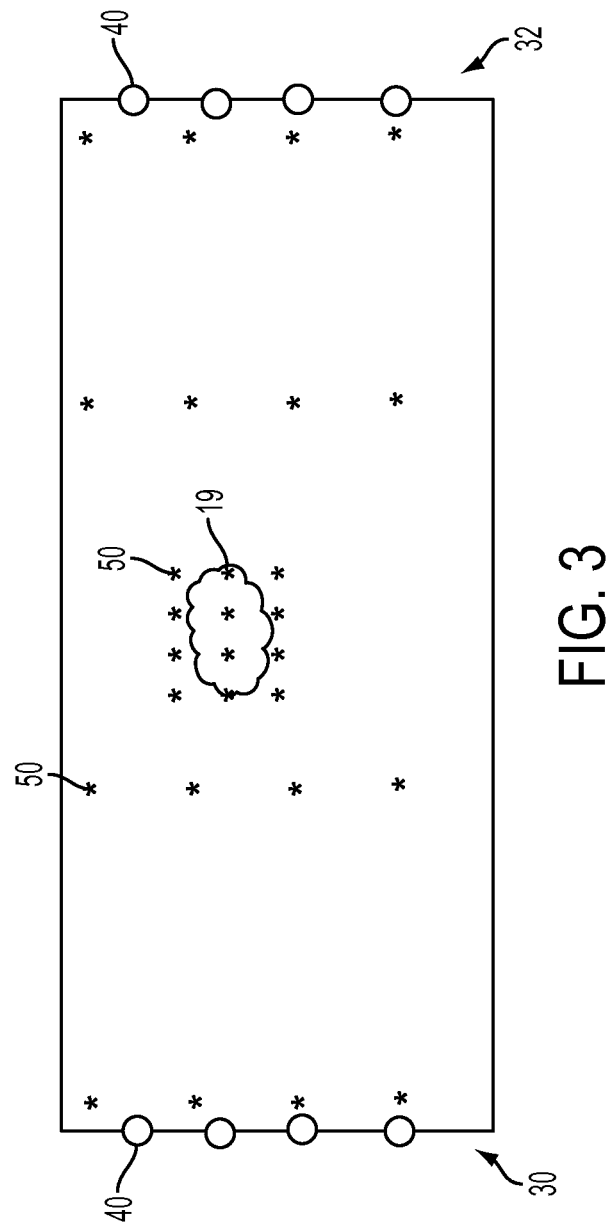
FIG. 3 is an unwrapped plan view of a two-dimensional model of the unwrapped pipe after the pulse-echo test.

Turning now to FIG. 3, the results of pulse-echo test are used to approximate a two-dimensional model of the unwrapped pipe 12. It is to be appreciated that the two-dimensional model of the unwrapped pipe 12 is somewhat generically/schematically depicted in FIG. 3 for illustrative purposes. In particular, the first transducer ring 30 (disposed on the left-most side of the two-dimensional model) and second transducer ring 32 (disposed on the right-most side of the two-dimensional model) are shown to include only four transducers 40. However, in operation and as set forth above, the first transducer ring 30 and second transducer ring 32 can each include more than four transducers 40. Moreover, the transducers 40 are generically depicted as circular points, however in operation, the transducers 40 further include structure such as a transmitter, receiver, etc.

Based on the results of the pulse-echo test, an approximate location of the characteristic 19 is determined and plotted on the two-dimensional model of the unwrapped pipe 12. To more accurately determine the size of the characteristic 19, points 50 can be plotted on the two-dimensional model of the pipe 12. In one example, the points 50 can represent a parameterization of the thickness of the pipe 12. For example, the density of the points 50 is adjusted based on the location of the characteristic 19. The points 50 can be relatively sparsely positioned at locations where characteristic 19 has not been detected. In particular, the points 50 are sparsely positioned near the first transducer ring 30, near the second transducer ring 32, etc. Likewise, the points 50 could be sparsely positioned at other locations between the first transducer ring 30 and second transducer ring 32 where the characteristic 19 has not been detected.

The points 50 are more densely positioned where the characteristic 19 has been detected by the pulse-echo test. For example, the points 50 can be more closely positioned to nearby points 50 in an area closely surrounding the characteristic 19. Indeed, as shown in FIG. 3, a series of points 50 (four points in the shown example) can be positioned on one side of the characteristic 19 while another series of points 50 (four points in the shown example) can be positioned on an opposing second side of the characteristic 19. Likewise, one or more points can be positioned on opposing longitudinal ends of the characteristic 19. Further still, one or more points may be positioned on (e.g., overlapping) the characteristic(s) 19. It is to be understood that the location of the points 50 shown in FIG. 3, including both the sparsely and densely positioned points, comprises only one of many possible locations. Indeed, any number of points 50 could be provided at any number of locations. Further, while only one characteristic 19 is shown, a plurality of characteristics 19 could be located within the pipe 12, such that multiple areas of high density points may be provided. The points 50 need not be organized in straight lines, and instead, could form staggered rows, columns, and/or random patterns.

Figure 4:
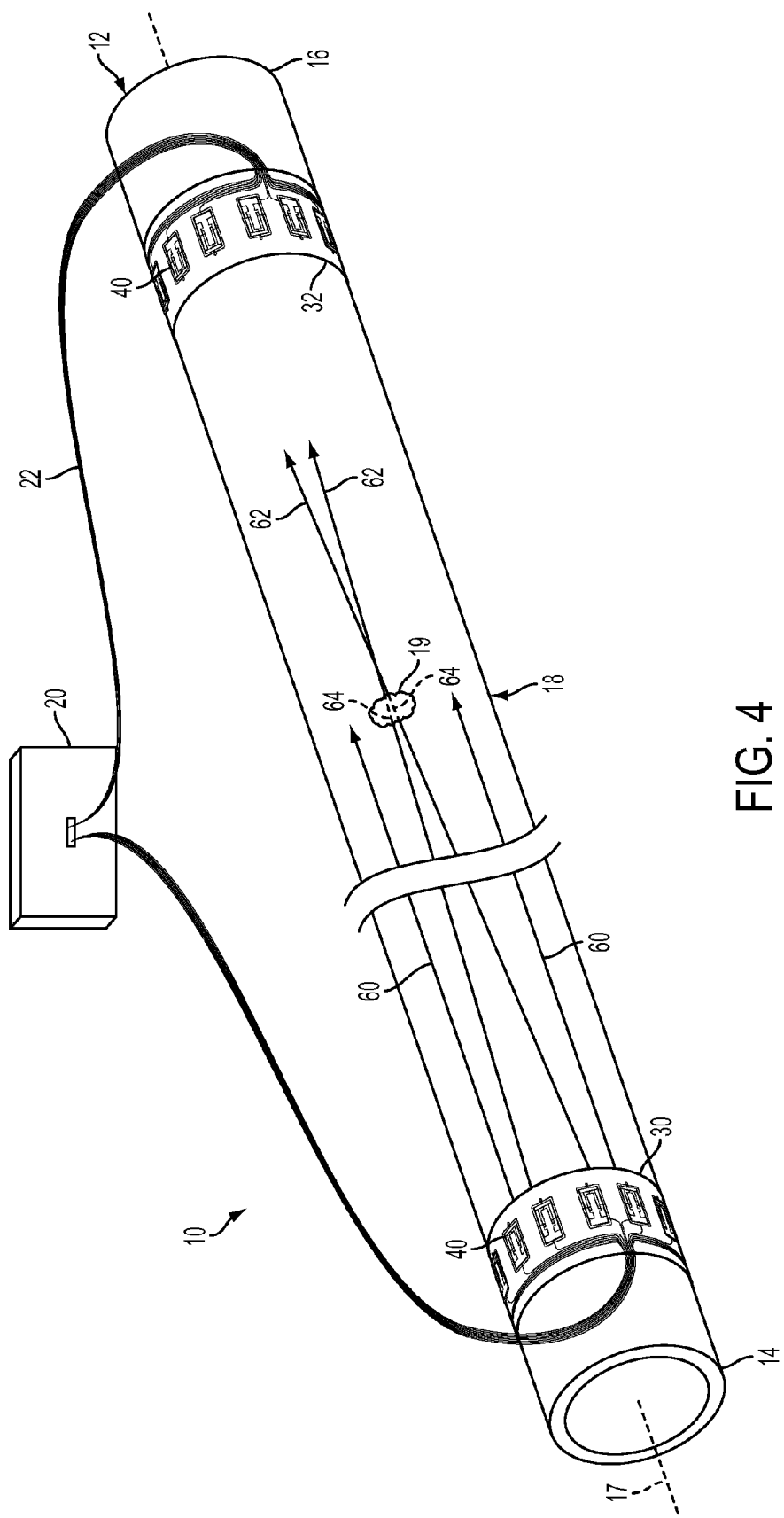
FIG. 4 is a perspective view of the example ultrasonic sensor assembly during a guided wave tomographic test.

Turning now to FIG. 4, the guided wave tomographic test can now be carried out to more accurately determine the size of the characteristic 19. In particular, the guided wave tomographic test can use the results of the pulse-echo test and the points 50 plotted in FIG. 3 to determine the size of the characteristic 19. In this example, the first transducer ring 30 will create and transmit one or more second waves 60 into the pipe 12 from the first transducer ring 30. The second waves 60 are guided towards the characteristic(s) 19 based on the results of the pulse-echo test. The second waves 60 can be transmitted by the transducers 40 into the inspection region 34. It is to be appreciated that the second waves 60 are somewhat generically depicted (as arrowheads) since the second waves 60 can include a pulse, energy, and/or other impulses.

The first transducer ring 30 can transmit the second waves 60 in nearly any order. For example, the transducers 40 of the first transducer ring 30 can each transmit second waves 60 individually. In such an example, one of the transducers 40 will transmit second waves 60 to generate a moderately dispersive guided wave. The guided wave are generally guided and aimed/targeted at a specific location (e.g., towards the characteristic 19). Next, another one of the transducers 40 will transmit second waves 60. This process can continue until some or all of the transducers 40 in the first transducer ring 30 have transmitted the second waves 60. In another example, at least some (or all) of the transducers 40 can simultaneously transmit the second waves 60.

The second waves 60 will propagate from the first transducer ring 30 into the inspection region 34. At least some of the second waves 60 can be directed towards the characteristic 19. In particular, based on the results of the pulse-echo test and the densely positioned points 50 (shown in FIG. 3) around the characteristic 19, the second waves 60 can be focused by the first transducer ring 30 towards the characteristic 19. As such, some of the second waves 60, depicted as affected waves 62, will pass through the characteristic 19, while other second waves 60 may not pass through the characteristic 19. In the shown example, the affected waves 62 include the second waves 60 that pass through the characteristic 19. As such, the affected waves 62 can each include an affected portion 64. The affected portion 64 (depicted as a dashed line) is the portion of the affected wave 62 that travels through the characteristic 19. This affected portion 64 can be affected by the characteristic 19, such as by altering (e.g., slowing down) the time of flight of the affected waves 62.

The second waves 60, including the affected waves 62 that pass through the characteristic 19, will propagate through the inspection region 34 and towards the second transducer ring 32. The second transducer ring 32 can function as a receiving ring and will receive the second waves 60, including the affected waves 62 that pass through the characteristic 19. It is to be appreciated that while FIG. 4 shows the first transducer ring 30 as the transmitting ring and the second transducer ring 32 as the receiving ring, the ultrasonic sensor assembly 10 is not so limited. Rather, in further examples, the second transducer ring 32 could act as the transmitting ring while the first transducer ring 30 acts as the receiving ring, such that the second waves 60 can travel in an opposite direction from the direction shown in FIG. 4.

The second waves 60, including the affected waves 62, are received by the transducers 40 of the second transducer ring 32. Information related to the affected waves 62 can then be transmitted to the test apparatus 20. The test apparatus 20 analyzes and evaluates characteristics related to the affected waves 62 and the second waves 60. For example, the test apparatus 20 can compare characteristics of the affected waves 62 with characteristics of the second waves 60. These characteristics can include, for example, a time of flight (e.g., arrival time), amplitude, velocity change, time shift, etc.

Based on this analysis and evaluation of the second waves, including the affected waves 62, the test apparatus 20 can draw conclusions as to the size of the characteristic 19. In one example, a tomographic method can be used to produce a velocity map of the pipe 12, which can then be converted into a thickness map of portions of the pipe 12. In particular, the test apparatus 20 can determine the size (e.g., longitudinal length, circumferential width, thickness, etc.) of the characteristic 19. For example, a time of flight for the affected waves 62 that pass through the characteristic 19 will be different from a time of flight for the second waves 60 that do not pass through the characteristic 19. In particular, the time of flight may be slower for the affected waves 62 received by the second transducer ring 32 than for the second waves 60. Since the location of the characteristic 19 has already been determined through the pulse-echo test, the size of the characteristic 19 can be obtained based on how large the difference in time of flight is between affected waves 62 and second waves 60. In a further example, as is generally known, the velocities of the second waves 60 and affected waves 62 can be related to dispersion curves such that a thickness map can be obtained of the pipe 12. As such, the guided wave tomographic test, along with the pulse-echo test, can accurately determine the presence/absence, location and the size of the characteristic 19 within the pipe 12.

By combining the pulse-echo test and the guided wave tomographic test, the presence/absence, location, and size of the characteristic 19 can be more accurately determined. In particular, the results of the pulse-echo test are used to determine the presence/absence and location of the characteristic 19 within the pipe 12. This information can then be used to augment the guided wave tomographic test to determine the size of the characteristic 19.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. An ultrasonic sensor assembly for detecting a characteristic of a pipe, the ultrasonic sensor assembly including:
    a first transducer ring encircled to circumscribe around the pipe and attached to the pipe;
    a second transducer ring encircled to circumscribe around the pipe and attached to the pipe at a spaced location from the first transducer ring; and
    a test apparatus operatively connected to the first and second transducer rings and being configured to communicate with the first and second transducer rings;
    each of the first and second transducer rings being configured to transmit a first wave longitudinally along the pipe and receive a reflection of the transmitted first wave from the characteristic, the test apparatus and the first transducer ring further being configured to use results related to the reflection of the transmitted first wave to guide a second wave along the pipe that is received by the second transducer ring.

2. The ultrasonic sensor assembly of claim 1, wherein the first transducer ring and second transducer ring are spaced apart along the pipe to define an inspection region extending between the first transducer ring and the second transducer ring.

3. The ultrasonic sensor assembly of claim 2, wherein the characteristic of the pipe is positioned within the inspection region.

4. The ultrasonic sensor assembly of claim 3, wherein the first and second transducer rings are each configured to transmit the waves in a direction towards the inspection region.

5. The ultrasonic sensor assembly of claim 1, wherein the first and second transducer rings each include a plurality of transducers configured to transmit the waves.

6. The ultrasonic sensor assembly of claim 5, wherein the plurality of transducers are configured to transmit the waves at substantially the same time.

7. The ultrasonic sensor assembly of claim 1, wherein the first and second transducer rings are configured to detect a circumferential location of the characteristic.

8. The ultrasonic sensor assembly of claim 7, wherein the first and second transducer rings are configured to detect an longitudinal location of the characteristic.

9. The ultrasonic sensor assembly of claim 8, wherein the characteristic includes corrosion.

10. The ultrasonic sensor assembly of claim 8, wherein the characteristic includes a crack in the pipe.

11. An ultrasonic sensor assembly for detecting a characteristic of a pipe, the ultrasonic sensor assembly including:
    a first transducer ring encircled to circumscribe around the pipe and attached to the pipe;
    a second transducer ring encircled to circumscribe around the pipe and attached to the pipe at a spaced location from the first transducer ring; and
    a test apparatus operatively connected to the first and second transducer rings and being configured to communicate with the first and second transducer rings;
    each of the first and second transducer rings being configured to transmit a first wave longitudinally along the pipe and receive a reflection of the transmitted first wave reflected from the characteristic, the test apparatus and the first transducer ring further being configured to use results related to the reflection of the transmitted first wave to guide a second wave along the pipe that is received by the second transducer ring;
    wherein the waves received by the transducer rings are configured to be analyzed to detect a dimension and location of the characteristic of the pipe.

12. The ultrasonic sensor assembly of claim 11, wherein the location of the characteristic of the pipe includes a circumferential location of the characteristic.

13. The ultrasonic sensor assembly of claim 11, wherein the location of the characteristic of the pipe includes a longitudinal location of the characteristic.

14. The ultrasonic sensor assembly of claim 11, wherein the characteristic includes corrosion of the pipe.

15. The ultrasonic sensor assembly of claim 11, wherein the first transducer ring and second transducer ring are spaced apart along the pipe to define an inspection region extending between the first transducer ring and the second transducer ring, the characteristic of the pipe being positioned within the inspection region.

16. The ultrasonic sensor assembly of claim 15, wherein the first and second transducer rings are each configured to transmit the waves in a direction towards the inspection region.

17. A method of detecting a characteristic of a pipe, the method including the steps of:
    providing an ultrasonic sensor assembly including first and second transducer rings attached to and spaced apart along a length of the pipe and including a test apparatus operatively connected to the first and second transducer rings and being configured to communicate with the first and second transducer rings;
    providing the first transducer ring encircled to circumscribe around the pipe;
    providing the second transducer ring encircled to circumscribe around the pipe;
    transmitting one or more first waves into the pipe from each of the first and second transducer rings;
    receiving a reflection of the one or more transmitted first waves reflected from the characteristic by the first and second transducer rings;
    transmitting one or more second waves into the pipe from the first transducer ring including using the reflection of the one or more transmitted first waves to guide the one or more second waves and receiving the one or more second waves with the second transducer ring; and
    detecting the characteristic of the pipe based on the waves received by each of the first and second transducer rings.

18. The method of claim 17, wherein the step of detecting the characteristic of the pipe includes detecting a circumferential location of the characteristic.

19. The method of claim 17, wherein the step of detecting the characteristic of the pipe includes detecting a longitudinal location of the characteristic.

20. The method of claim 17, wherein the step of detecting the characteristic of the pipe includes detecting dimensions of the characteristic.

* * * * *